United States Patent
Pingleton et al.

[11] Patent Number: 6,117,150
[45] Date of Patent: Sep. 12, 2000

[54] PNEUMATIC TISSUE DISSECTOR WITH EXHAUST SYSTEM

[75] Inventors: Edward D. Pingleton, Fillmore; Gary L. Butler, Bloomington; Neal E. Fearnot, West Lafayette; Donald R. Hollinger, Bloomington, all of Ind.; Timothy G. Vendrely, Milwaukee, Wis.; Ralph V. Clayman, Clayton, Mo.

[73] Assignees: Cook Urological Incorporated, Spencer; MED Institute, Inc., West Lafayette, both of Ind.

[21] Appl. No.: 09/115,008

[22] Filed: Jul. 14, 1998

Related U.S. Application Data

[60] Provisional application No. 60/052,420, Jul. 14, 1997.

[51] Int. Cl.[7] .................................................. A61B 17/32
[52] U.S. Cl. ........................ 606/167; 606/190; 606/107; 604/35
[58] Field of Search .................................... 606/167, 165, 606/166, 190, 191, 192, 107, 170; 604/35, 33, 34, 143, 22, 24; 285/148.23; 128/898

[56] References Cited

U.S. PATENT DOCUMENTS

| | | |
|---|---|---|
| 4,913,698 | 4/1990 | Ito et al. . |
| 4,950,238 | 8/1990 | Sullivan . |
| 4,957,492 | 9/1990 | McVay . |
| 5,022,414 | 6/1991 | Muller . |
| 5,135,482 | 8/1992 | Neracher . |
| 5,573,504 | 11/1996 | Dorsey, III . |

*Primary Examiner*—Michael Buiz
*Assistant Examiner*—Lien Ngo
*Attorney, Agent, or Firm*—Richard J. Godlewski

[57] ABSTRACT

A pneumatic tissue dissector 10 useful for cutting or dissecting living tissue during endoscopic or laparoscopic procedures includes a dissector tip 16 for exuding a flow of pressurized gas, an inlet arrangement 24 for controlling the flow of gas from the tip 16, and an exhaust system 30 for exhausting the gas exuded from the tip 16. The exhaust system includes an inlet 32 adjacent to the tip 16 and an outlet spaced from the inlet 32. The outlet 34 is operable in coordination with the inlet arrangement 24 and is capable of exhausting a flow of gas about equal to that exuded by the tip 16, ensuring that the pressure in the cavity in which the procedure is performed does not increase or fluctuate. The flow of pressurized gas from the tip 16 is preferably compatible with an insufflation cavity pressure of no more than about 15 mm Hg, and the inlet arrangement 24 preferably supplies gas to the tip 16 at a pressure of no more than about 50 psi. The dissector 10 preferably further includes a laparoscopic introducer sheath 68 which is shorter in length than the distance between the inlet 32 and the outlet 34.

24 Claims, 8 Drawing Sheets

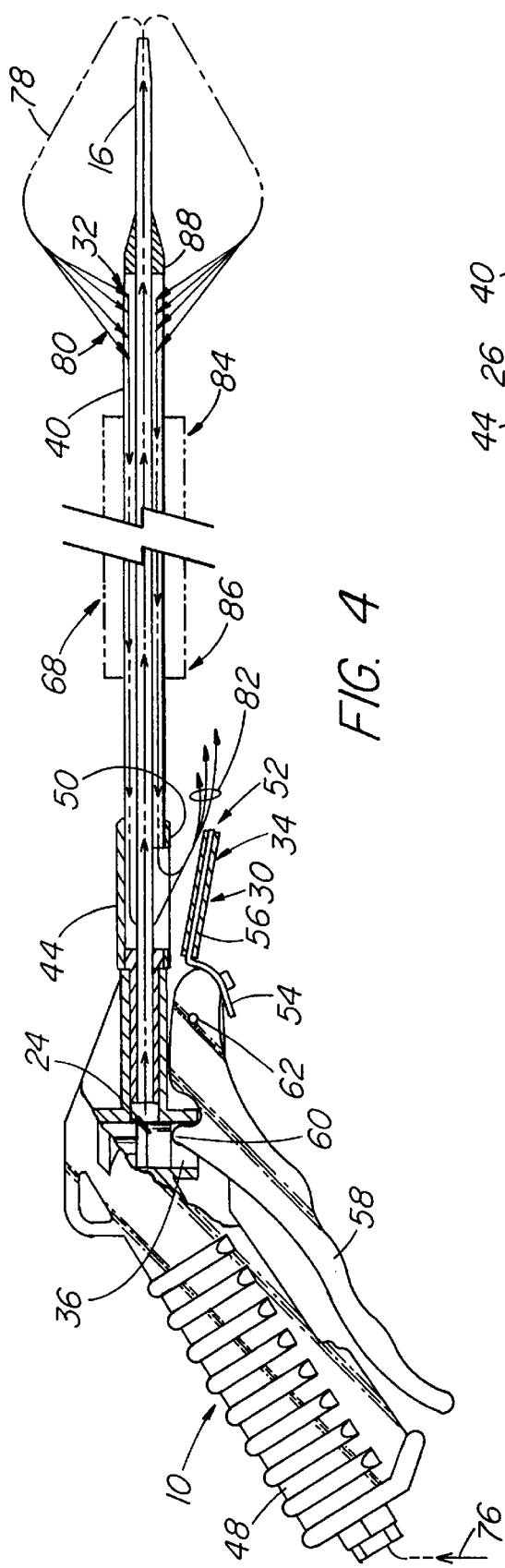
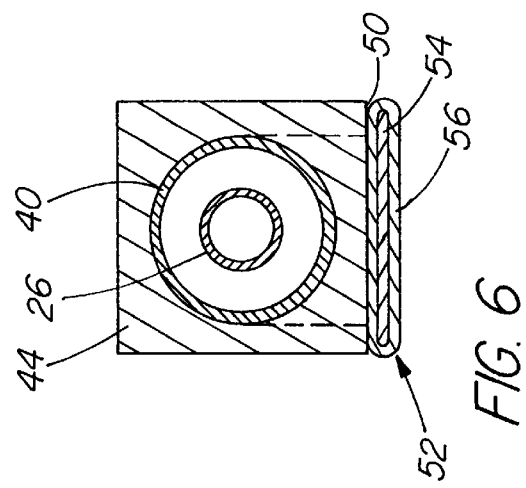
FIG. 4
FIG. 6
FIG. 5

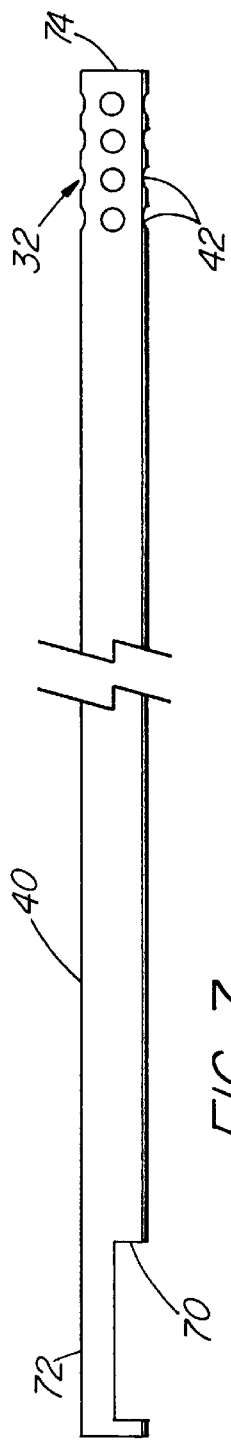
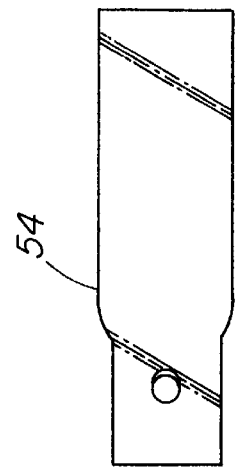
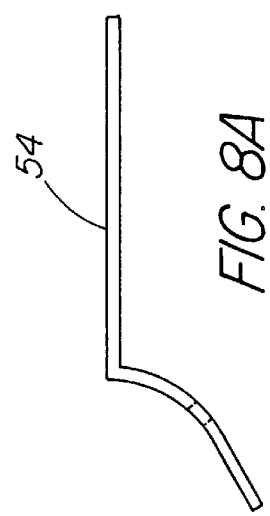
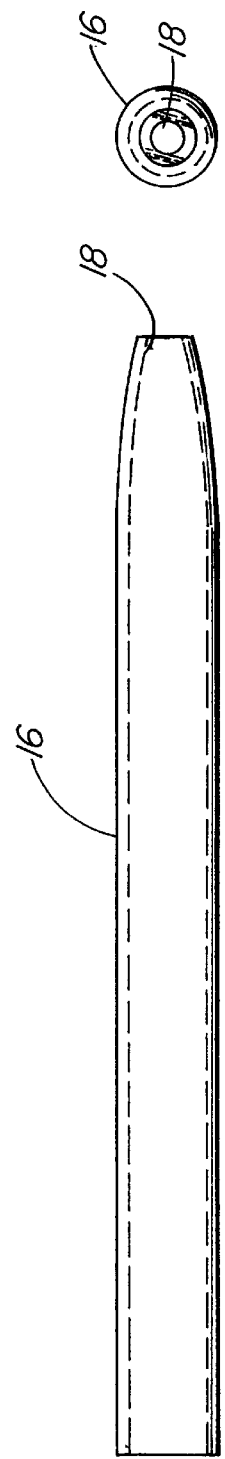
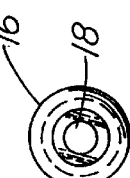

PNEUMATIC TISSUE DISSECTOR WITH EXHAUST SYSTEM

CROSS-REFERENCE TO RELATED APPLICATIONS

This application claims priority of provisional application Ser. No. 60/052,420, filed Jul. 14, 1997.

TECHNICAL FIELD

This invention relates generally to surgical devices, and more particularly to devices for cutting or dissecting living human or animal tissues.

BACKGROUND OF THE INVENTION

Despite advances in surgical instruments, and despite advances in the level of skill possessed by surgeons, procedures such as laparoscopy, endoscopy and the like are still plagued by significant disadvantages in comparison to traditional open surgical procedures. One of these disadvantages is the relatively lengthy operative times needed to perform laparoscopic and endoscopic procedures. A factor contributing significantly to such relatively long operative times is the lack of a laparoscopic instrument for safely and effectively performing rapid blunt-tissue dissection. Blunt-tissue dissection includes the separation of tissues such as tumor sacs or membranes from surrounding healthy tissue.

Numerous instruments exist for performing blunt tissue dissection in open surgical procedures. Such instruments are most often held in the hand of the surgeon and typically include a cutting and/or nudging apparatus which must actually contact the tissue to be separated. Such instruments have also included vibrating heads, physical nudging apparatus or scalpels. Unfortunately, the use of ultrasonic vibrating heads often entails the use of cumbersome umbilical connections to nearby generators (generally large enough to be floor mounted) with electrical power inputs of which such equipment can be very expensive. Alternatively, the use of scalpels can cause undesired damage to and bleeding from the tissue being separated. Moreover, the use of these and other instruments has required an extreme degree of care, and patience and delicate manipulation are necessary in their use if trauma to the patient is to be minimized. These problems are multiplied by the restricted movement and limited visibility encountered during laparoscopy, endoscopy and similar closed procedures.

Other problems exist with dissection techniques used in laparoscopy, endoscopy and the like. Laparoscopic graspers and scissors can be used to identify a target tissue plane and to separate the desired structure from tissues such as surrounding fat and overlying fascia. Because such instruments are rigid, because they generally develop tissue planes slowly and because they provide relatively poor tactile feedback (such tactile feedback is often referred to as "feel"), their use can result in the inadvertent creation of false tissue planes. Moreover, the natural tissue planes are sometimes not recognized. The result is the possibility that the surgeon can become disoriented during the procedure, and unintentionally damage non-targeted organs or tissue.

Some of these drawbacks can be overcome by the use of hydrodissection. Hydrodissection uses a pressurized fluid (such as water or saline solution), typically at about 700 mm Hg (roughly about 1 atm), to develop natural tissue planes. A jet of pressurized fluid moves along the path of least resistance through the tissue with relatively little trauma to the surrounding tissue and structures. Once the natural tissue planes are developed, conventional laparoscopic graspers and scissors are used to complete the procedure. Hydrodissection, however, has several limitations, including an undesirably low dissecting pressure, the creation of fluid laden tissues, the pooling of fluid in the insufflated cavity in the patient and the need to periodically evacuate the pooled dissecting fluid. The suctioning of pooled dissecting fluid from the insufflated cavity may, of course, result in the partial or total collapse of the insufflated cavity, if not carried out carefully. Such suctioning, of course, adds to the time required for performing the procedure, and draws the attention of the surgeon from the procedure itself.

The use of devices including electrosurgical cutters or lasers for tissue dissection is also subject to many of these drawbacks. Some of these devices require irrigation during use, so that the problem of the pooling of fluid remains. Moreover, such devices often produce smoke during their use, which interferes with the surgeon's view of the operative cavity, and which (like dissecting fluid) must be suctioned from the cavity.

Pressurized gas has been used to separate animal tissues, for example, for assisting in the skinning of an animal. U.S. Pat. No. 4,118,830 (Weiland, Oct. 10, 1978) discloses a hand-held device for this purpose. It has also been suggested to use pressurized gas for the surgical separation of tissues. For example, U.S. Pat. No. 4,357,940 (Muller, Nov. 9, 1982), U.S. Pat. No. 4,709,697 (Muller, Dec. 1, 1987) and U.S. Pat. No. 5,022,414 (Muller, Jun. 11, 1991) are all directed to a pneumatic tissue separator and method for using the same which includes a floating tip, through and/or around which gas (such as medical grade carbon dioxide) or liquid may be passed in order to separate tissue or clear previously separated tissue. The last of these patents notes in passing (at column 13, lines 36–44) that the device disclosed in it can be used as an adjunct in endoscopy, bronchoscopy, proctoscopy, sigmoidoscopy or arthroscopy. However, none of these patents discloses or suggests either the recognition of or the solution of a significant problem which may arise during the use of a pneumatic tissue separator in an insufflated cavity, in particular, the undesirable increase in cavity pressure which results from the introduction of the dissecting gas into the cavity.

It has been noted that this rise in pressure in the cavity, for example, a rise in intraperitoneal pressure, can be rapid; M. S. Pearle et al., "Laparoscopic Pneumodissection: Results in Initial 20 Patients," *J. Amer. Coll. Surg.*, 1997; 184:579–83. The article notes that intraperitoneal pressure can be maintained at 15 mm Hg or less by intermittent desufflation through the side arm of a laparoscopic port. Such a release of pressure can be rapid as well; M. S. Pearle et al., "Laparoscopic Pneumodissection: Initial Clinical Experience," *Urology*, 1995; 45:882–85. Unfortunately, the need to continually monitor cavity pressure and the need to manually release excess pressure through a laparoscopic port side arm can undesirably draw the attention of the surgeon away from the procedure being performed. It has been suggested that positioning an available pop off valve in line with the insufflation tubing, attached to the side arm of the port, can achieve this same purpose; S. M. Gardner et al., "Laparoscopic Pneumodissection: A Unique Means of Tissue Dissection," *J. Urol.*, 1995; 154:591–94. Such a valve would open whenever the cavity pressure, for example, the intraabdominal pressure, exceeded 16 mm Hg. The use of such a valve could be expected to have several drawbacks, however. The positioning of the valve in the side arm of a laparoscopic port prevents the side arm from being used for other purposes. Essentially, this requires the perforation of the patient with an additional laparoscopic sheath. It is of course highly desirable that a minimum number of sheaths be used during laparoscopic and endoscopic procedures. Moreover, pop off valves and the like are subject to failure and significant variations in operating tolerance, and can be stuck closed at pressures higher than intended. Further, it may take a small but perhaps appreciable time for pressures at different locations within the insufflated cavity to equalize, especially in a dead end structure such as a port side arm. This might undesirably delay release of pressure at the pop off valve. Of greatest concern may be that intracavital pressure cycles up and down between actuations of the pop off valve, with a resultant cyclic variation in the volume of the insufflated cavity. This not only distracts the surgeon but may cause relative movement of other operative instruments.

It would be highly desirable to have a tissue dissector which reliably prevented the build up of pressure in an insufflated surgical cavity. It would also be highly desirable to have a tissue dissector which achieved this prevention automatically, without requiring the attention of the surgeon to either continuous monitoring or to manual pressure release. It would also be desirable to have a tissue dissector which achieved higher dissection pressures than obtained with hydrodissection, yet which avoided the need to suction liquid or smoke from an insufflated surgical cavity. It would further be highly desirable to have a tissue dissector which did not risk trauma to visceral organs or blood vessels during normal use, as is possible with lasers, scalpels and other cutting devices. Of course, it should go without saying that it would also be desirable to achieve these objects at a relatively low cost, in particular, while avoiding the expensive equipment costs associated with ultrasonic cutters.

SUMMARY OF THE INVENTION

The foregoing problems are solved and a technical advance is achieved in an illustrative pneumatic tissue dissector which is particularly useful for cutting or dissecting tissues in an insufflated cavity, for example, during laparoscopic or endoscopic surgery or the like. The pneumatic tissue dissector of the present invention includes a distal end for exuding pressurized gas, an inlet arrangement for controlling the flow of pressurized gas from the distal end, and an exhaust system for removing excess gas from the region of the distal end. The exhaust system includes an outlet operable with the inlet arrangement. The exhaust system outlet also advantageously controls the application of suction to the region and/or the release of excess pressure from the region. The exhaust system can also comprise an exhaust channel extending from an exhaust system inlet or inlets adjacent the distal end to a control valve of the exhaust system outlet, the control valve serving to connect the exhaust channel to a lower pressure environment. The inlet arrangement can also comprise a gas inlet valve connected to the distal end and for connection to a gas supply. Accordingly, the control valve can be operable in coordination with the gas inlet valve.

In another aspect, the pneumatic tissue dissector of the present invention includes a tip for exuding a flow of pressurized gas for cutting or dissecting tissue, and an exhaust system whose operation is coordinated with the gas supplied to the dissector tip. More particularly, the gas is supplied through an inlet arrangement, and operation of the exhaust system is coordinated with operation of the inlet arrangement so that the inlet arrangement and the exhaust system are either both open or both closed at the same time, and so that the exhaust system is capable of exhausting a flow of gas about equal to the flow supplied through the inlet arrangement and exuded out the dissector tip. By way of example, the inlet arrangement can include a gas inlet valve or an on/off switch for controlling the gas flow.

The present invention is particularly advantageous over the prior art in that such coordinated operation of the inlet arrangement and the exhaust system reliably, affirmatively and automatically prevents the undesired build-up of pressure in the insufflation cavity while the dissector is in use, while simultaneously preventing the collapse of the cavity from over-venting. Intracavity pressure and cavity volume does not cycle up and down as might be the case if the cavity pressure was reduced by a pop off valve, and the surgeon need not fear a failure of the exhaust system to open, in contrast to the use of a pop off valve. Moreover, the present invention is expected to result in significant cost savings for two reasons. First, because the pneumatic tissue dissector of the present invention reduces the time needed to perform surgical procedures, in contrast to non-pneumatic devices, significant operating room charges can be avoided. Second, the pneumatic tissue dissector of the present invention is relatively low in cost to manufacture. Its cost can be only 5 to 10 percent of the dollar value of the time and operating room charges its use saves, so that the dissector can in some cases be considered to be disposable. Further, the present invention avoids the misidentification of tissue planes because it operates at pressures several times higher than the pressures used in hydrodissectors. The present invention also avoids the pooling of liquids in the insufflated cavity associated with the use of hydrodissectors and the like, and does not require the suction needed to remove the smoke produced by electrosurgical cutters and by lasers.

The pneumatic tissue dissector of the present invention finds use in a variety of procedures; a small number of examples of such procedures include expanding the perirenal space, dissecting perirenal fat from the surface of the kidney, dissecting perihilar tissue from the renal vessels, kidney and renal hilar dissection, dissection of the retroperitoneum, laparoscopic nephroureterectomy, laparoscopic pelvic lymph node dissection, laparoscopic nephrectomy (simple, bilateral or radical), renal cyst decortication, nephropexy, pyeloplasty, ureterolysis, pelvic cyst excision, and elevating or otherwise mobilizing tissues or organs.

In a first aspect, then, the present invention is directed to a pneumatic tissue dissector comprising: a dissector tip for exuding a flow of pressurized gas; an inlet arrangement for controlling the flow of pressurized gas from the dissector tip; and an exhaust system comprising an inlet adjacent to the dissector tip, and an outlet operable in coordination with the inlet arrangement.

Preferably, the tissue dissector of the present invention further comprises a conduit fluidly connecting the dissector tip to the inlet arrangement, and the exhaust system further comprises a hollow shaft surrounding the conduit. Also preferably, the exhaust system inlet is formed as a plurality of transverse perforations through the hollow shaft.

The tissue dissector of the present invention can conveniently include a handle carrying the inlet arrangement and the exhaust system outlet. Each of these can be operatively connected to a trigger carried on the handle, so that each can only be operated simultaneously with the other, upon movement of the trigger. Since the shaft perforations are positioned adjacent to the dissector tip, up and down cycling of intracavity pressure and cavity volume, or delays in the venting of gas pressure caused by operation of the dissector, are affirmatively prevented. The pneumatic tissue dissector of the present invention can also comprise a variety of other desirable elements, as described in more detail below.

In a second aspect, the present invention is directed to a device of the type disclosed above, comprising a specific combination of such elements. In particular, in its second aspect the present invention is directed to a pneumatic tissue dissector comprising: a dissector tip for exuding a flow of pressurized gas; an inlet arrangement for controlling the flow of pressurized gas from the dissector tip; a conduit fluidly connecting the dissector tip to the inlet arrangement, the dissector tip being rigidly connected to the conduit; an exhaust system comprising an inlet adjacent to the dissector tip, an outlet operable in coordination with the inlet arrangement, and a hollow shaft disposed parallel to and surrounding the conduit; a handle carrying the inlet arrangement and the exhaust system outlet, the exhaust system outlet comprising a seat formed in the handle; a trigger carried on the handle and operatively connected to the inlet arrangement and exhaust system outlet, the trigger abutting the inlet arrangement; and a laparoscopic introducer sheath through which the dissector tip and the inlet are insertable, the introducer sheath being shorter than the distance between the exhaust system inlet and the outlet; wherein the exhaust system inlet is formed as a plurality of transverse perforations through the hollow shaft; wherein the flow of pressurized gas exuded from the dissector tip is compatible with an insufflation cavity pressure of no more than about 15 mm Hg; wherein the inlet arrangement supplies gas to the dissector tip at a pressure of no more than about 50 psi; wherein the exhaust system is capable of venting a flow of gas about equal to the flow of pressurized gas exuded by the dissector tip; wherein the exhaust system outlet comprises a member carried by the trigger and sealingly engageable with the seat in the handle; and wherein the dissector tip defines a circular orifice having a cross-sectional area of about 6.7 $mm^2$.

The various aforementioned embodiments can also include a variety of enhancements to further extend its surgical utility. These include a dissector tip that is interchangeable, deflectable, and/or adjustable for improving access to surgical sites or providing different gas flow patterns for dissecting tissue. An electrosurgical or optical element can also be included about the dissector tip to aid in cutting or coagulating tissue. Medicants and the like can also be advantageously introduced into a patient by including an injector or simply a venturi and feeder tube for supplying the materials to be sprayed by the gas flow. A multiple position valve can also be included in the inlet arrangement to individually select a gas flow, aspiration, or irrigation line that can be readily attached to just one dissector to speed up the surgical procedure.

In a final aspect, the present invention is directed to a method of using a pneumatic tissue dissector comprising a dissector tip for exuding a flow of pressurized gas, an inlet arrangement for controlling the flow of pressurized gas from the dissector tip, and an exhaust system comprising an inlet adjacent to the dissector tip and an outlet operable in coordination with the inlet arrangement; and the method comprising the steps of: establishing an insufflated cavity; positioning the dissector tip and the exhaust system inlet in the insufflated cavity; and actuating the inlet arrangement so as to exude a flow of pressurized gas from the dissector tip and out the exhaust system outlet. Preferably, the method comprises the further step of positioning a laparoscopic introducer sheath across the insufflated cavity, and the step of positioning the dissector tip and the exhaust system inlet comprises introducing the dissector tip and the exhaust system inlet through the laparoscopic introducer sheath.

Again, as noted above, the pneumatic tissue dissector of the present invention possesses an enormous number of advantages over prior tissue dissecting devices.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 4 is a partial cross-sectional view similar to FIG. 3, showing the flow of gas during operation of the preferred embodiment of the present invention;

FIG. 5 is a bottom view of a portion of the preferred embodiment of the present invention;

FIG. 6 is a cross-sectional view taken along line 6—6 of FIG. 3;

FIG. 7 is a side view of a portion of the preferred embodiment of the present invention;

FIGS. 8A and 8B are side and bottom views, respectively, of another portion of the preferred embodiment of the present invention;

FIGS. 9A and 9B are side and end views, respectively, of still another portion of the preferred embodiment of the present invention.

DETAILED DESCRIPTION

Figure 1:
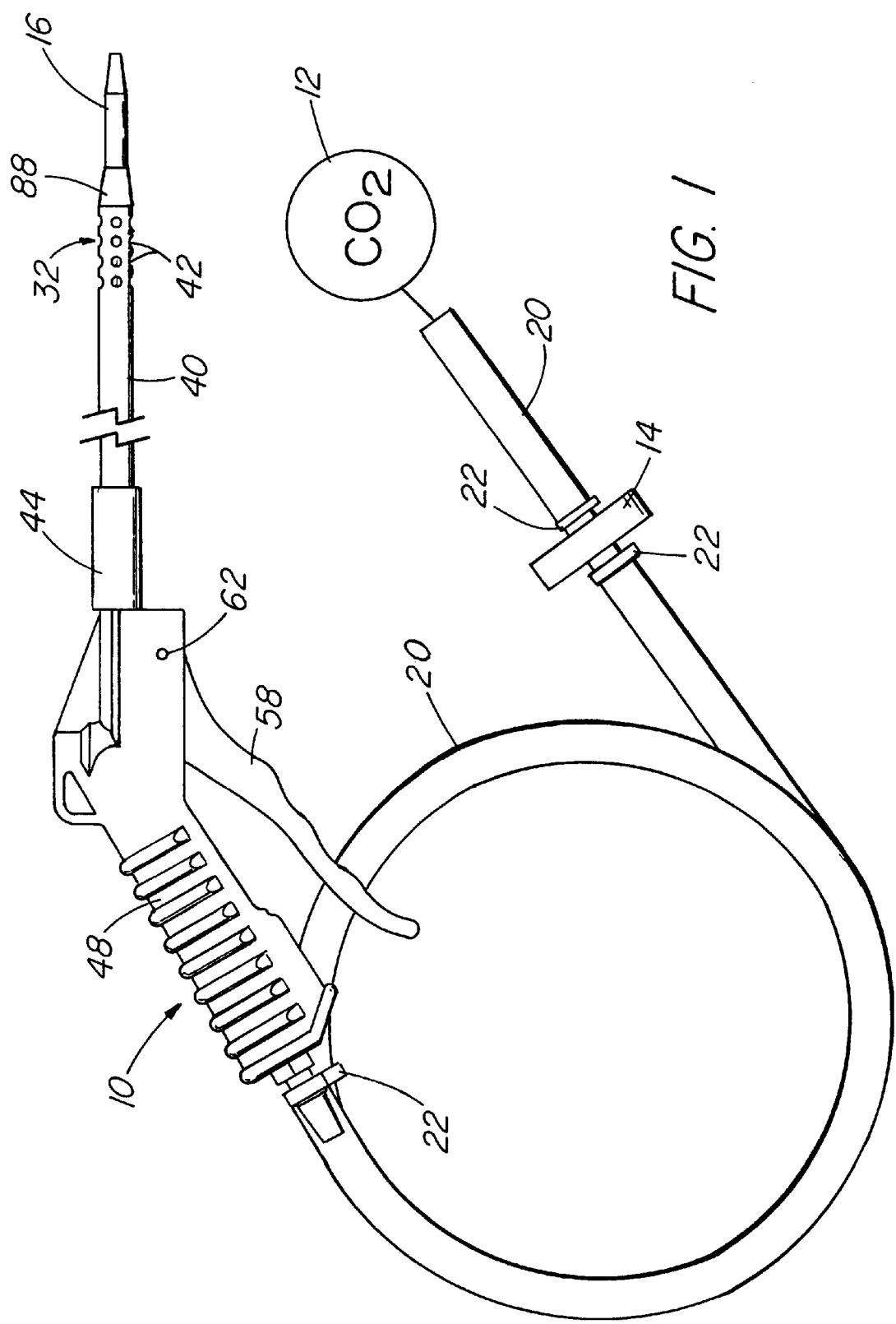
FIG. 1 is a side view of the preferred embodiment of the present invention.
Figure 2:
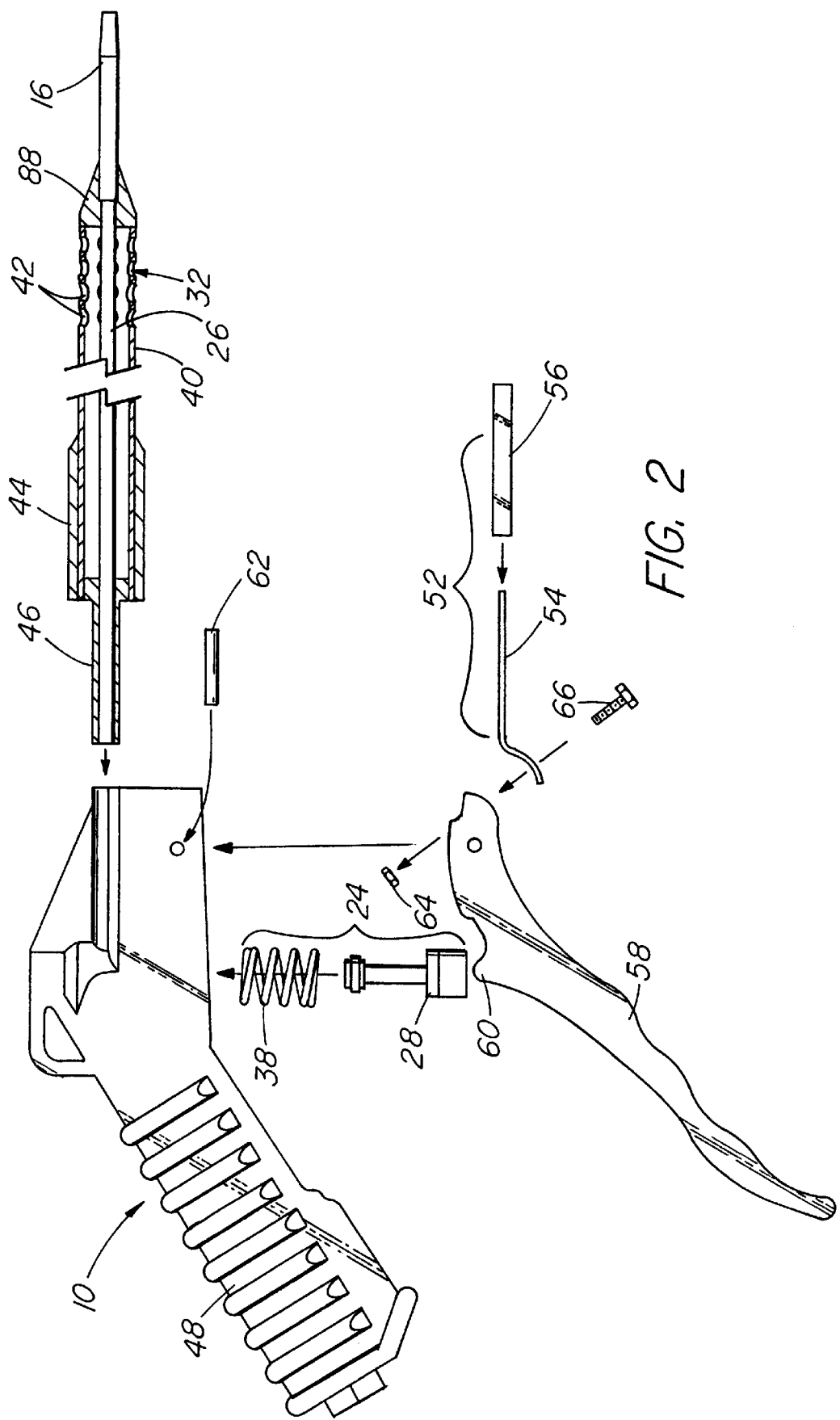
FIG. 2 is an exploded view of the preferred embodiment of the present invention.

With reference first to FIGS. 1 and 2, a pneumatic tissue dissector 10 according to the present invention is thereshown and first comprises a supply 12 of a gas suitable for use in an insufflated cavity inside a human or veterinary patient. The gas supply 12 can be pulsed or continuous, and the gas supplied by the gas supply 12 is preferably the same gas as that employed for establishing and maintaining the insufflated cavity in the patient. The gas supply 12 is preferably a source of medical grade carbon dioxide gas. The dissector 10 also comprises a graspable handle 48 adapted to allow the pressurized gas to pass through it, for example, through a passage (not shown) formed in the handle 48. A conventional gas filter 14 is positioned between the gas supply 12 and the handle 48, and the filter 14, the gas supply 12 and the handle 48 are fluidly connected by a plurality of hoses 20 fixed in position by a plurality of suitable clamps 22. The gas filter 14 removes any undesired contaminants, oils or the like from the gas supplied by the gas supply 12.

The pneumatic tissue dissector 10 of the present invention also includes a distal end 16 or a dissector tip 16 receivable in an insufflated cavity within a patient. The dissector tip 16 is for exuding a flow of pressurized gas supplied from the gas supply 12 having sufficient strength to perform the desired cutting or dissecting of tissue within the insufflated cavity. A preferred shape for the dissector tip 16 is shown in FIGS. 9A and 9B. The dissector tip 16 preferably defines an exit orifice 18 which is circular in cross-section. The dissector tip 16 and its orifice 18 can be otherwise shaped as desired to facilitate the cutting or dissecting of particular tissues, but a circular cross-section can be most useful for general dissecting purposes. At normal operating pressures, that is, at pressures no more than about 50 psi, and preferably about 46 to 47 psi, the exit orifice 18 can conveniently have a cross-sectional area of about 6.7 mm$^2$. The size of the orifice 18 can be varied, however, to facilitate the performance of specific dissecting procedures.

Figure 17:
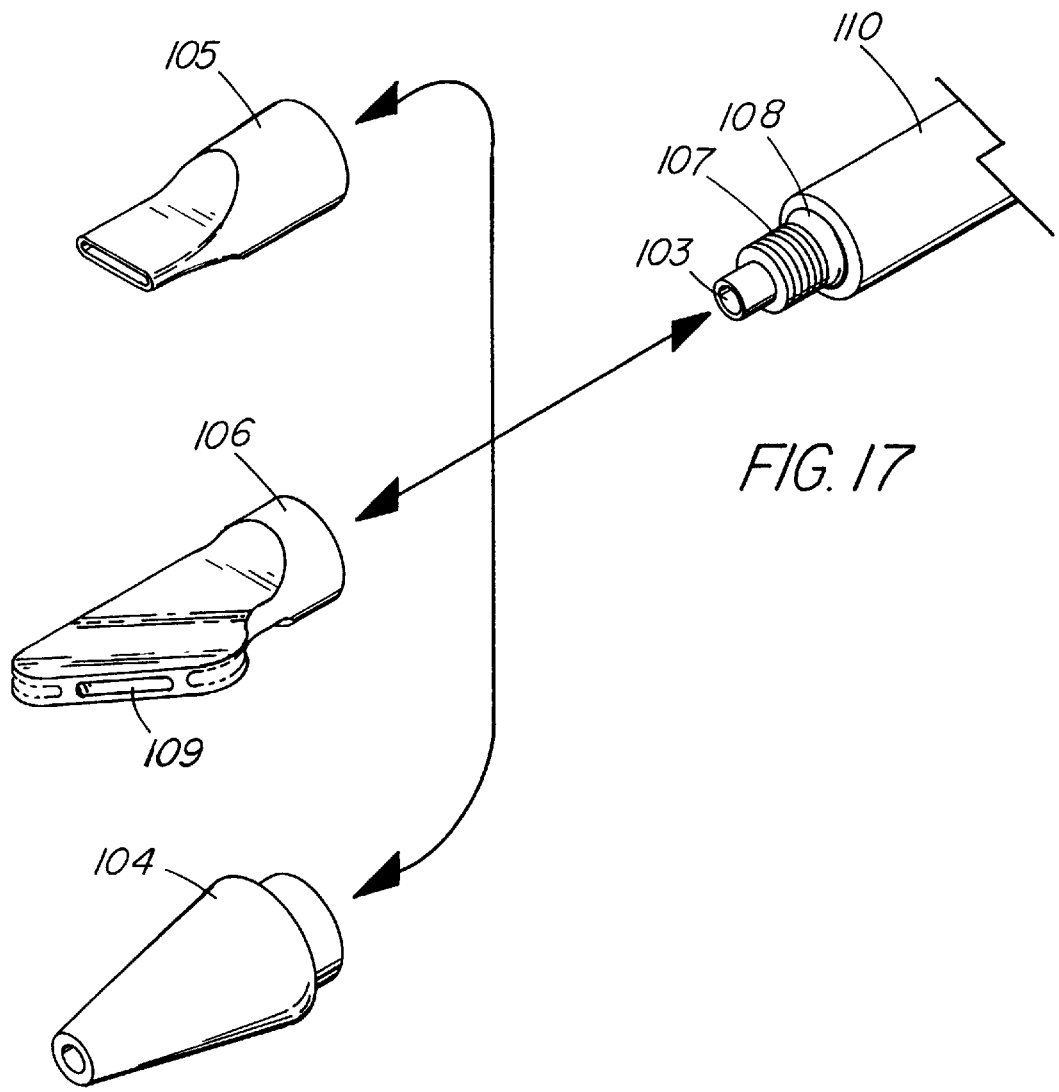
FIG. 17 is pictorial view of an eighth alternative embodiment of the present invention.

In an alternative embodiment of the dissector of the present invention depicted in FIG. 17, the distal end or dissector tip can include a plurality of interchangeable and detachable tips 104–106 that readily mount (thread) on shaft 110 of the dissector. These interchangeable tips include round dissection tip 104 for concentrated flow and tissue cutting, planar dissection tip 106 with an elliptical orifice for blunt dissection, and cutting tip 106 with one or more angled elliptical orifices 109.

Figure 3:
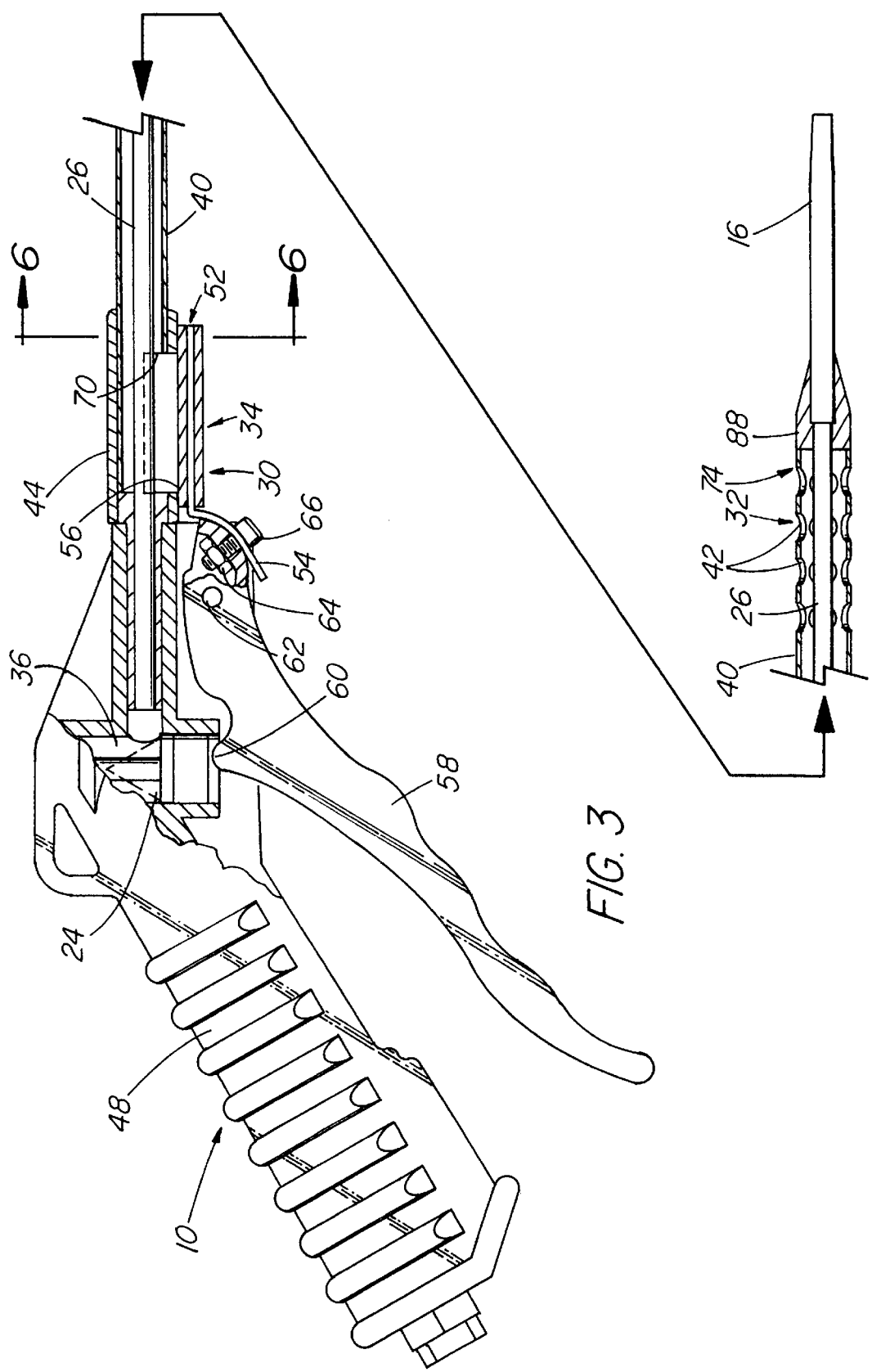
FIG. 3 is a partial cross-sectional view taken in the plane of FIG. 1.

The dissector 10 of the present invention further comprises an inlet arrangement 24 including a gas inlet valve carried by the handle 48 for controlling the flow of pressurized gas from the gas supply 12, to and thereby from the dissector tip 16. The gas valve 24 is conveniently formed from a valve element 28 received in a recess 36 formed in the handle 48 (FIG. 3). A spring 38 biases the valve element 28 to a closed position. The gas inlet valve 24 can be a valve which supplies gas continuously while it is open, or can be a valve which supplies a single pulse of gas when it is opened, depending upon the dissection procedure to be performed. Preferably, the gas supply 12 and the gas valve 24 cooperate to provide a flow of pressurized gas exuded from the dissector tip which is compatible with an insufflation cavity pressure of no more than about 25 to 30 mm Hg, preferably, no more than about 15 mm Hg.

The tissue dissector 10 additionally comprises an exhaust system 30 which automatically exhausts and/or releases an amount of gas from the insufflated cavity about equal to that introduced into the insufflated cavity by the dissector tip 16. More particularly, the exhaust system 30 comprises an exhaust system inlet 32 positioned adjacent to the dissector tip 16, which is positionable within the insufflated cavity, and an exhaust system outlet 34 spaced from the inlet 32. The outlet 34 is operable in coordination with operation of the inlet arrangement and, in particular, the gas inlet valve 24. "In coordination with" means that either or both of two conditions is met: (a) that the outlet 34 operates at the same time as the inlet arrangement or gas inlet valve 24 operates; or (b) that operation of the outlet 34 exhausts or releases an amount of gas from the insufflated cavity sufficient to prevent an undesirable cycling or increase in intracavital pressure from the dissection performed by the dissector tip 16, without exhausting or releasing so much gas that a threat is presented to maintaining a constant volume for the insufflated cavity.

Preferably, the tissue dissector 10 of the present invention further comprises a conduit 26 fluidly connecting the dissector tip 16 to the inlet arrangement or gas inlet valve 24. The exhaust system 30 further comprises a hollow shaft 40 disposed parallel to and surrounding the conduit 26. The exhaust system inlet 32 is conveniently formed as at least one transverse perforation 42 through the shaft 40, located near the distal end 74 of the shaft 40. Preferably, a plurality of perforations 42 are provided extending around the distal end 74 of the shaft 40. Also preferably, the dissector tip 16 is rigidly connected to the conduit 26 and to the distal end 74 of the shaft 40 by a connector 88 to which each is connected, for example, by welding. As previously described, the dissector tip can also be fashioned to be interchangeable such as with tips 104–106 depicted in FIG. 17.

The handle 48 includes a valve body 44 and a joint sleeve 46 for joining the conduit 26 and the hollow shaft 40 to the handle 48. The tissue dissector 10 further comprises a trigger 58 carried on the handle 48 and operatively connected to the inlet arrangement or gas inlet valve 24 and the exhaust system outlet valve 34. The trigger 58 is pivotably connected to the handle 48 by a pivot pin 62.

The exhaust system outlet 34 is conveniently carried on the handle 48 and first comprises a seat 50 formed in the handle 48, in particular, in the body 44. The shaft 40 includes a cut-out or notch 70 (FIG. 7) in registry with the seat 50. The relation of the notch 70 and the seat 50 is shown in FIG. 5. The outlet 34 further comprises an exhaust system valve member 52 connected to the trigger 58 by a nut 64 and machine screw 66. The valve member 52 sealingly engages the seat 50. More particularly, the valve member 52 comprises a generally rigid but partly curved plate 54 (FIGS. 8A and 8B) carrying on it a resilient seal 56 formed, for example, as an elastic band encircling a flat portion of the plate 54. The trigger 58 moves the seal 56 into and out of engagement with the seat 50 so as to close or open the exhaust system outlet 34. The relative positions of the valve member 52 and the seat 50 when the outlet 34 is closed is shown in FIG. 6. The trigger 58 includes a projection 60 abutting the inlet arrangement or gas inlet valve 24, so that movement of the trigger 58 also actuates the gas inlet valve 24. Thus, the opening or closing of the exhaust system 30 is necessarily coordinated with the actuation of the gas inlet valve 24, and thereby with the exuding of pressurized gas from the dissector tip 16.

The pneumatic tissue dissector 10 of the present invention preferably further comprises a laparoscopic introducer sheath 68 through which the dissector tip 16 and the exhaust system inlet 32 are insertable, so that the dissector tip 16 and the inlet 32 are positionable within an insufflated cavity established in a human or veterinary patient. The introducer sheath 68 is shown only schematically in FIG. 4 and can be of any conventional or convenient construction. The introducer sheath 68 must, of course, be shorter than the distance between the exhaust system inlet 32 and the outlet 34, so that the shaft 40 is capable of passing gas from inside the insufflated cavity to outside the insufflated cavity.

The preferred method of use of the pneumatic tissue dissector 10 of the present invention to cut or dissect tissue can now be readily understood. An insufflated cavity is first established in a human or veterinary patient in any conventional manner. Those skilled in this area should be fully familiar with techniques for establishing and maintaining such a cavity, and fully aware of the requisites for protecting patient safety during the practice of such techniques. The dissector tip 16 and the exhaust system inlet 32 are then positioned in the insufflated cavity. Preferably, a laparoscopic introducer sheath 68 is positioned across the insufflated cavity with its distal end 84 located in the cavity and its proximal end 86 lying outside the cavity. The positioning of the dissector tip 16 and the inlet 32 in the cavity is then carried out by introducing the tip 16 and inlet 32 through the introducer sheath 68. The inlet arrangement or gas inlet valve 24 is then actuated (for example, by movement of the trigger 58) so as to exude a flow of pressurized gas from the dissector tip 16 for cutting or dissecting tissue within the cavity, the pressurized gas then passing through the perforations 42 into and through the hollow vent shaft 40, and out the vent outlet valve 34 (opened by the same movement of the trigger 58 that actuated the gas inlet valve 24). Arrows 76–82 in FIG. 4 indicate the flow of gas into and out of the tissue dissector 10 during its use.

Although neither necessary nor preferred, the exhaust system 30 (and, in particular, the outlet 34) could be connected to a source of suction or negative pressure to hasten the venting of gas from the insufflated cavity. There might be some surgical circumstances under which such an arrangement would have advantages, but again, such an arrangement is not preferred in the practice of the present invention.

The tissue dissector 10 of the present invention should, of course, be composed of medical grade materials which can be sterilized by conventional procedures prior to use. Conveniently, the dissector 10 can be made of relatively inexpensive synthetic and metallic materials, so that the dissector 10 can be disposed of after a single use, rather than being resterilized and reused. Such reuse, however, is also contemplated within the scope of the invention.

Several details of the construction of the dissector 10 of the present invention may facilitate its inexpensive manufacture and/or its successful use. The hoses 20 connecting the gas supply 12, the filter 14 and the handle 48 may be ⅜ inch diameter PVC hose or other suitable hose. The filter 14 is conveniently a commercially available 0.3 micron filter. The handle 48 can be composed of an acetal material. The total length of the hoses 20 between the gas supply 12 and the handle 48 should be sufficient to allow the operating room source of carbon dioxide gas to serve as the gas supply 12, so that the total length of the hoses 20 can conveniently be about 12 feet. For common laparoscopic applications, the total length of the tip 16, conduit 26 and shaft 40 from the tip orifice 18 to the valve body 44 is conveniently about 32 cm±1 cm. The shaft 40, conduit 26 and dissector tip 16 can all be composed of stainless steel. The tip 16 itself can be composed of 6.5 GHW stainless steel tubing about 2.20 in.±0.01 in. long, with a taper on its distal 0.020 in.±0.002 in. to yield a preferred inner diameter for the orifice 18 of about 0.115 in. (2.92 mm). The preferred proportions are shown in FIGS. 9A and 9B. The shaft 40 can be composed of stainless steel tubing having an inner diameter of 0.355 in. and an outer diameter of 0.375 in., and a total length of about 12.00 in.±0.02 in. The perforations 42 through the shaft 40 can conveniently have a diameter of 0.150 in. The notch 70 begins 0.100 in. from the opposite end of the shaft 40 and is about 1.100 in. long. The interior of the valve body 44 is dimensioned accordingly. Finally, the exhaust system plate 54 is conveniently shaped in the proportions shown in FIGS. 8A and 8B. The handle 48 is also commercially available as part of a 205 series blow gun from Cejn Industrial Corp., Gurnee, Ill.

Figure 10:
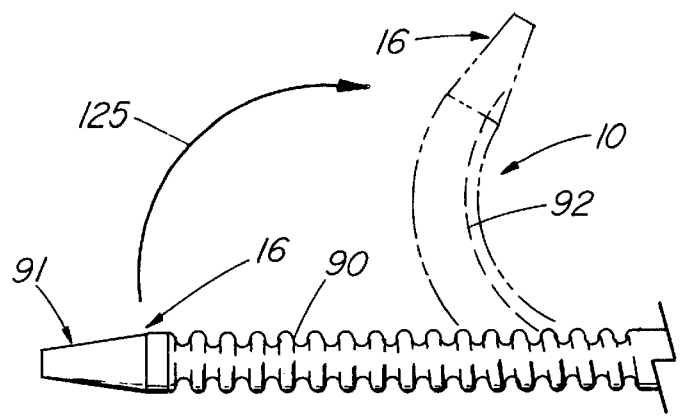
FIG. 10 is a side view of a portion of an alternative embodiment of the present invention.

FIGS. 10–17 depict a series of alternative embodiments of the present invention. A modification of the pneumatic tissue dissector tip 16 is shown in FIG. 10 whereby this distal portion is made deflectable to approach a target structure at different angles to facilitate dissection. This particular embodiment has flexible portion 90 just proximal to the distal end 91 of the tip that is, for example, corrugated to permit the tip to be manually deflectable to obtain a desired deflection within the patient. Deflection of the tip can occur once inside the patient or prior to introduction into the body. Ideally, the tip should be able to be deflected at least 120° to reach normally inaccessible areas. For example, safe and effective dissection around a renal artery or vein would require the ability to deflect the tip in order to dissect behind and around these delicate structures.

The second embodiment of FIG. 10, which is represented by the phantom lines, includes a tip that is deflectable by means of a remotely-operated control member 92 such as a wire or string running the length of tip which is made flexible by the material used or the structure of the flexible portion. The amount of tension to applied to the control member determines the degree of the angle of tip deflection.

Figure 11:
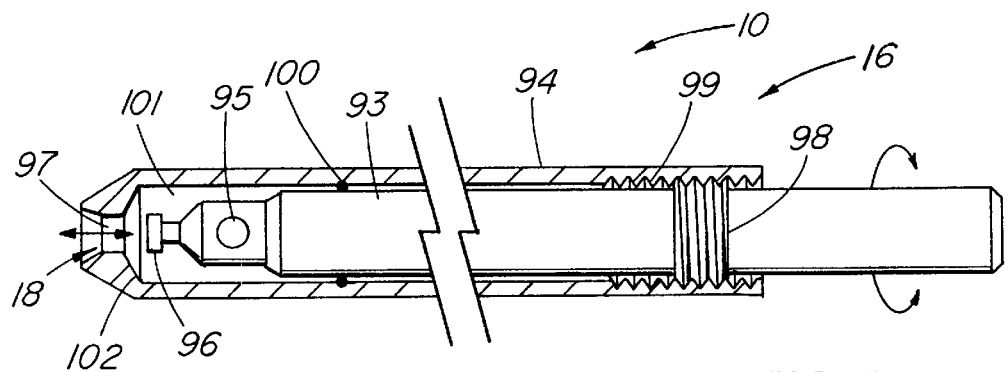
FIG. 11 is a partially sectioned side view of a second alternative embodiment of the present invention.

FIG. 11 depicts another alternative embodiment of the present invention that includes an adjustable dissector tip 16 capable of adjusting the amount and/or pattern of the exuded gas or gas flow. The distal portion of the pneumatic tissue dissector 10 is comprised of an inner member 93 and an adjustable outer sleeve 94. Gas flows through the inner member, exiting via a side port 95 located proximal to distal end 96 of the inner member. The gas then enters an air space 101 between the inner member and an outer member and where it is forced through a short channel 97 and out the tip orifice 18 at the distal end of the outer sheath. The outer sheath includes an internal threaded portion 99 which engages an external threaded portion on the inner member. This allows the inner member to advance or retract relative to the outer member as the outer member is rotated. Advancement of the inner member eventually results in the distal end 96 of the inner member sealing the channel 97 between the air space 101 and the tip orifice 18. The air space is sealed proximally by an O-ring 100. As the advancing distal end 96 of the inner member nears the proximal edge 102 of the channel 97, the stream of gas becomes less focused and is expelled with less velocity. A broad pattern of gas is better suited for blunt dissection, whereas a concentrated flow would be better for more precise cutting of tissue.

Alternative methods of adjusting the stream of flow include having a the gas exit from the distal end of the inner member having a distal orifice of a first diameter. The distal orifice of the outer member has a second, smaller diameter. As the outer member is retracted, the distal orifice of the outer member enlarges to broaden the stream of gas flow. This can be accomplished by the inner member causing a series of leaves surrounding the outer member orifice to spread, increasing the diameter of the outer member orifice.

FIG. 17 depicts yet other alternative embodiments of the present tissue dissector invention in which the size and pattern of the gas stream is varied by the use of different interchangeable and detachable tips 104–106. The distal orifice 103 of the proximal shaft 110 is connected to any one of a variety of different pneumatic dissector tip 16 configurations. Tips configurations 104, 105, 106 can be threaded onto the external threads 107 of the tip shaft 103. A few of the possible tip configurations include a round orifice tip 104 for concentrated flow for cutting through tissue. A flattened tip 105 is more useful for blunt dissection to separate tissue. Another flattened tip design 106 includes one or more exit ports 109 along the narrow edge of the paddle-shaped distal portion. This results in the tip acting like a scalpel when cutting tissue. An O-ring 108 seated at the proximal end of the threaded portion 107 of the shaft, prevents leakage of gas when the detachable tip is in place. Alternative structures for attaching the replaceable tips of the distal tip include a bayonet or other locking means.

Figure 12:
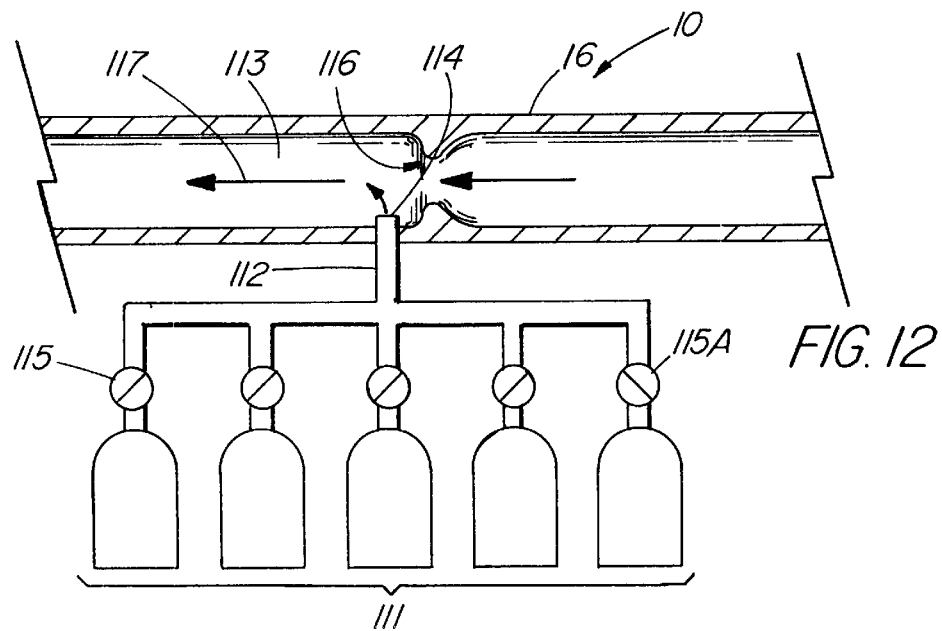
FIG. 12 is a partially sectioned side view of a portion of third alternative embodiment of the present invention.

FIG. 12 depicts still yet another alternative embodiment of the present pneumatic dissector invention that includes a means of delivering a selection of one or more medicants, materials, gases, etc. within the patient. A series of vials 111 each having a valve 115 feed into a common tube 112. The outlet 116 of the feeder tube 112 enters into the lumen 113 of the dissector tip 16 and occurs at a point 116 just distal to a venturi 114 within the lumen. Gas flowing through the venturi creates a venturi effect whereby the lowered pressure distal to the venturi allows the medicants, material, gases, etc. to be drawn from the vial, introduced into the stream of gas 117, and sprayed from the dissector tip orifice. Thus, medicants and the like are introduced into a patient. The effect is very similar to that of paint being sprayed from a spray gun. One example of a material for this application would be fibrin glue to seal an anastomosis (e.g., pyeloplasty, vascular), seal a cut surface of a parenchymal structure (e.g., kidney, liver, spleen), or to stop an area of diffuse bleeding, such as that following dissection. Other uses for the device would include spraying growth factors to stimulate healing or anastomosis, heparin solution in patients with malignancies to preclude seeding of malignant cells, and small intestinal submucosa (SIS) at the port sites to preclude help prevent scar formation.

Figure 13:
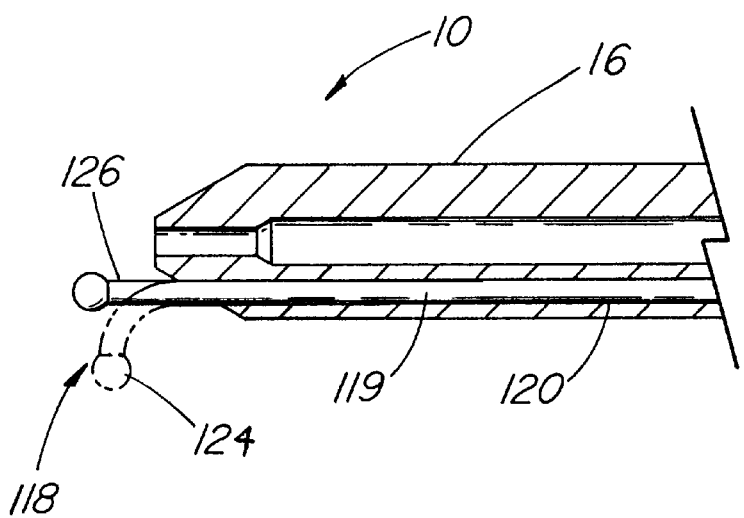
FIG. 13 is a partially sectioned side view of a fourth alternative embodiment of the present invention.

FIG. 13 depicts a alternative embodiment of the pneumatic tissue dissector 10 in which the tip of the device includes an electrosurgical probe or element 118 that assumes the shape of a right angle hook 123 as it is advanced out of a lumen 119 in the wall 120 of the dissector's hollow tip 16. The configuration of the hook is such that as tissue is bluntly dissected, any uncovered small vessels are immediately electrocoagulated and divided. This provides the capability for rapid and bloodless dissection.

Figure 14:
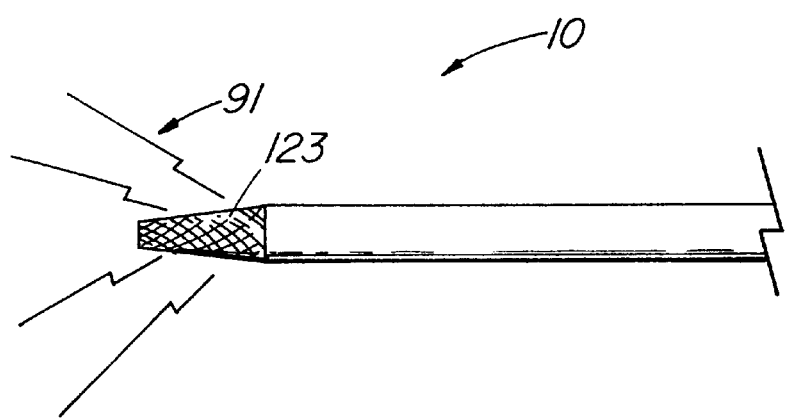
FIG. 14 is a side view of a fifth alternative embodiment of the present invention.

FIG. 14 depicts another method for adding electrosurgical capabilities in which the distal tip 91 itself is electrified so that it can also function as an electrosurgical probe when current is supplied under the control of the operator. A further modification of the pneumatic tissue dissector is shown in FIG. 14, whereby the distal tip 91 has a roughened surface 123 to aid with blunt mechanical dissection.

Figure 15:
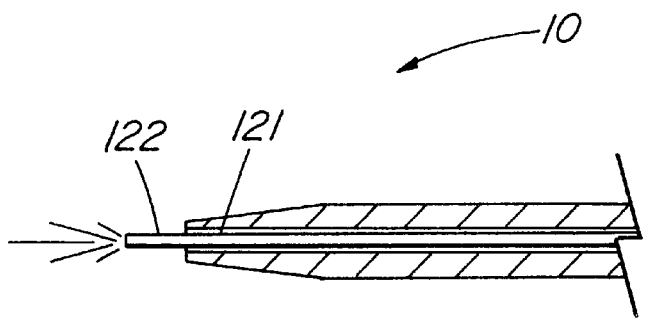
FIG. 15 is a sectioned sided view of a sixth alternative embodiment of the present invention.

FIG. 15 depicts another alternative embodiment of the present invention that includes a central passageway 121 that can accommodate an optical fiber 122, such as for transmitting Holmium laser light for cutting and/or coagulation. The passageway diameter must be at least 500 microns to accommodate a typical laser fiber.

Figure 16:
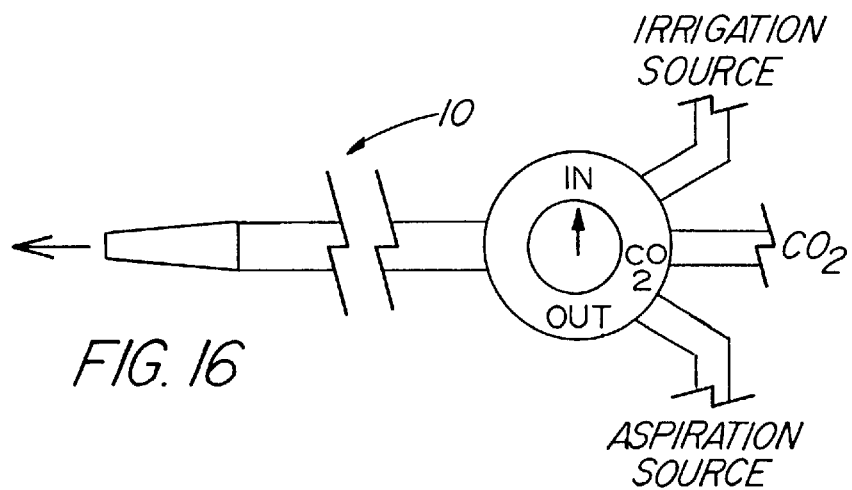
FIG. 16 is a schematic view of a seventh alternative embodiment of the present invention.

FIG. 16 depicts a schematic view of an alternative embodiment that includes a triple stopcock or three way valve that permits switching the incoming/outgoing line between the $CO_2$ source for pneumatic dissector; a pump for aspirating blood or smoke resulting from electrocautery; and an irrigation system for introducing saline or other solutions to clear blood from the field, or to introduce medicants such as an antibiotic solution. A combinational pneumatic tissue dissector with these additional capabilities eliminates the need and expense of a separate irrigator/aspirator system.

Of course, these and the other details of construction can be changed to adapt the pneumatic tissue dissector 10 of the present invention to the particular surgical technique to be performed.

It should be clear from the foregoing disclosure that the pneumatic dissector 10 of the present invention is particularly advantageous over prior devices in a variety of ways. Most importantly, the coordinated operation of the gas inlet valve and the exhaust system reliably, affirmatively and automatically prevents the undesired build-up of pressure in the insufflation cavity while the dissector is in use, while simultaneously preventing the collapse of the cavity from over-exhausting. Intracavity pressure and cavity volume do not cycle up and down as might be the case if the cavity pressure was reduced by a pop off valve, and the surgeon need not fear a failure of the exhaust system outlet of the present invention to open, in contrast to the use of a pop off valve. Moreover, the present invention is expected to result in significant cost savings, because it reduces the time needed to perform surgical procedures and is relatively low in cost to manufacture. Further, because it operates at pressures several times higher than the pressures used in hydrodissectors, the risk of misidentification of tissue planes during its use is substantially reduced. The present invention also avoids the pooling of liquids in the insufflated cavity associated with the use of hydrodissectors and the like, and does not require the suction needed to remove the smoke produced by electrosurgical cutters or lasers.

The details of the construction or composition of the various elements of the tissue dissector 10 not otherwise disclosed are not believed to be critical to the achievement of the advantages of the present invention, so long as the elements possess the strength or flexibility needed for them to perform as disclosed. It should be remembered, however, that the individual Figures are proportionate representations of the preferred embodiment of the present invention, or portions of it, with dimensions as indicated in the detailed description given above. The selection of any other details of construction are believed to be well within the ability of one of even rudimentary skills in this area, in view of the present disclosure.

Industrial Applicability

The present invention is useful in the performance of surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A pneumatic tissue dissector comprising:
    a dissector tip (16) for exuding a flow of pressurized gas;
    an inlet arrangement (24) for controlling the flow of pressurized gas from the dissector tip; and
    an exhaust system (30) comprising an inlet (32) adjacent to the dissector tip and an outlet (34) operable with the inlet arrangement.

2. The dissector (10) according to claim 1, further comprising a conduit (26) fluidly connecting the dissector tip (16) to the inlet arrangement (24), wherein the exhaust system (30) further comprises a hollow shaft (40) disposed parallel to the conduit (26).

3. The dissector (10) according to claim 2, wherein the hollow shaft surrounds the conduit (26).

4. The dissector (10) according to claim 2, wherein the inlet is formed as at least one transverse perforation (42) through the hollow shaft (40).

5. The dissector (10) according to claim 1, wherein the dissector tip (16) is rigidly connected to the conduit (26).

6. The dissector (10) according to claim 1, further comprising a gas supply (12) connected to the inlet arrangement (24).

7. The dissector (10) according to claim 1, wherein the flow of pressurized gas exuded from the dissector tip (16) is compatible with an insufflation cavity pressure of no more than about 15 mm Hg.

8. The dissector (10) according to claim 1, wherein the inlet arrangement (24) supplies gas to the dissector tip (16) at a pressure of no more than about 50 psi.

9. The dissector (10) according to claim 1, wherein the exhaust system (30) is capable of exhausting a flow of gas about equal to the flow of pressurized gas exuded by the dissector tip (16).

10. The dissector (10) according to claim 1, further comprising a handle (48) carrying the inlet arrangement (24) and the outlet (34).

11. The dissector (10) according to claim 10, wherein the outlet (34) comprises a seat (50) formed in the handle (48).

12. The dissector (10) according to claim 10, further comprising a trigger (58) carried on the handle (48) and operatively connected to the inlet arrangement (24) and the outlet (34), the trigger (58) abutting the inlet arrangement (24).

13. The dissector (10) according to claim 12, wherein the outlet (34) comprises a seat (50) formed in the handle (48), and a member (52) carried by the trigger (58) and sealingly engageable with the seat (50).

14. The dissector (10) according to claim 1, wherein the dissector tip (16) defines an orifice (18) having a cross-sectional area of about 6.7 mm$^2$.

15. The dissector (10) according to claim 1, wherein the dissector tip (16) defines an orifice (18) having a circular cross-section.

16. The dissector (10) according to claim 1, further comprising a laparoscopic introducer sheath (68) through which the dissector tip (16) and the inlet (32) are insertable, the introducer sheath (68) being shorter than the distance between the inlet (32) and the outlet (34).

17. A dissector according to claim 1, wherein the distal end (16) includes an interchangeable dissector tip (104–106).

18. A dissector according to claim 1, wherein the distal end (16) includes a deflectable dissector tip (16) having a flexible portion.

19. A dissector according to claim 1, wherein the distal end (16) includes an adjustable dissector tip (16) for adjusting the amount and/or pattern (10) of the exuded gas.

20. A dissector according to claim 1, wherein the dissector further includes a venturi (114) and feeder tube (112) for introducing one or more medicants into a patient.

21. A dissector according to claim 1, wherein the distal end includes an electrosurgical element (118).

22. A dissector according to claim 1, wherein the dissector includes an optical fiber (122).

23. A dissector according to claim 1, wherein the dissector further includes a multiple position valve connected to the inlet arrangement.

24. A pneumatic tissue dissector (10) comprising:

a dissector tip (16) for exuding a flow of pressurized gas;

an inlet arrangement (24) for controlling the flow of pressurized gas from the dissector tip (16);

a conduit (26) fluidly connecting the dissector tip (16) to the inlet arrangement (24), the dissector tip (16) being rigidly connected to the conduit (26);

an exhaust system (30) comprising an inlet (32) adjacent to the dissector tip (16), an outlet (34) operable in coordination with the inlet arrangement (24), and a hollow shaft (40) disposed parallel to and surrounding the conduit (26);

a handle (48) carrying the inlet arrangement (24) and the outlet (34), the outlet (34) comprising a seat (50) formed in the handle (48);

a trigger (58) carried on the handle (48) and operatively connected to the inlet arrangement (24) and the outlet (34), the trigger (58) abutting the inlet arrangement (24); and a laparoscopic introducer sheath (68) through which the dissector tip (16) and the inlet (32) are insertable, the introducer sheath (68) being shorter than the distance between the inlet (32) and the outlet (34);

wherein the inlet (32) is formed as a plurality of transverse perforations (42) through the hollow shaft (40);

wherein the flow of pressurized gas exuded from the dissector tip (16) is compatible with an insufflation cavity pressure of no more than about 15 mm Hg;

wherein the inlet arrangement (24) supplies gas to the dissector tip (16) at a pressure of no more than about 50 psi;

wherein the exhaust system (30) is capable of exhausting a flow of gas about equal to the flow of pressurized gas exuded by the dissector tip (16);

wherein the outlet (34) comprises a member (52) carried by the trigger (58) and sealingly engageable with the seat (50) in the handle (48); and wherein the dissector tip (16) defines a circular orifice (18) having a cross-sectional area of about 6.7 mm$^2$.

* * * * *